US012678608B1

(12) United States Patent
Wang et al.

(10) Patent No.: US 12,678,608 B1
(45) Date of Patent: Jul. 14, 2026

(54) MICRONEEDLING DEVICE

(71) Applicant: Huizhou Xinminghong Technology Co., Ltd, Huizhou (CN)

(72) Inventors: Li Wang, Leizhou (CN); Hongcheng Wang, Leizhou (CN)

(73) Assignee: Huizhou Xinminghong Technology Co., Ltd, Huiyang (CN)

( * ) Notice: Subject to any disclaimer, the term of this patent is extended or adjusted under 35 U.S.C. 154(b) by 0 days.

(21) Appl. No.: 19/356,241

(22) Filed: Oct. 13, 2025

(30) Foreign Application Priority Data

Jul. 16, 2025 (CN) .......................... 202530417020.8
Sep. 3, 2025 (CN) .......................... 202521894602.6

(51) Int. Cl.
*A61M 37/00* (2006.01)
(52) U.S. Cl.
CPC . *A61M 37/0015* (2013.01); *A61M 2037/0023* (2013.01); *A61M 2037/0046* (2013.01); *A61M 2202/0007* (2013.01); *A61M 2202/04* (2013.01); *A61M 2210/04* (2013.01)
(58) Field of Classification Search
CPC ...... A61M 37/0015; A61M 2037/0023; A61M 2037/0046; A61M 2202/0007; A61M 2202/04; A61M 2210/04
See application file for complete search history.

(56) References Cited

U.S. PATENT DOCUMENTS 5,746,365 A * 5/1998 Scott .......................... A45F 3/00
224/684
10,967,163 B1 * 4/2021 Groop ............... A61M 37/0015

FOREIGN PATENT DOCUMENTS

CN 216091866 U 3/2022
CN 216571184 U 5/2022
CN 114588525 A 6/2022

* cited by examiner

*Primary Examiner* — Bhisma Mehta
*Assistant Examiner* — Haden Matthew Ritchie
(74) *Attorney, Agent, or Firm* — Nitin Kaushik

(57) ABSTRACT

The invention relates to cosmetic treatment devices, and discloses a microneedling device, which includes a handle with a liquid medicine cavity, a main cavity, a stamp assembly with a detachable bottom shell, a microneedle assembly with micro-needles with detachable bases and a telescopic control device. The control device uses a rotating sleeve to achieve precise extension and retraction of the microneedle, which can be adapted to skin drug delivery in multiple scenarios and improve flexibility of use.

7 Claims, 14 Drawing Sheets

MICRONEEDLING DEVICE

CROSS-REFERENCE TO RELATED APPLICATIONS

The application claims priority to Chinese patent application No. 2025304170208, filed on Jul. 16, 2025, and Chinese patent application No. 2025218946026, filed on Sep. 3, 2025, the entire contents of which are incorporated herein by reference.

TECHNICAL FIELD

The invention relates to the field of cosmetic treatment devices, in particular, to a microneedling device.

BACKGROUND

In the field of skin drug administration, microneedling technology is widely used in scenarios such as freckle removal, acne removal, and skin repair because it can break through the stratum corneum barrier of the skin and increase the penetration rate of liquid medicines. The accuracy in controlling the extension and retraction of microneedles for existing microneedling devices is low, and most of them adopt a simple press-type structure. It is difficult to adjust the extension length of the microneedle according to skin thickness and requirements in drug administration, which can easily cause excessive skin damage or insufficient introduction of liquid medicine.

SUMMARY

In view of the above description, an objective of the invention is to provide a microneedling device to solve the defects of existing microneedling devices.

A microneedling device of the solution includes:

a handle, which is a handheld operating component with a liquid medicine cavity arranged inside therein along an axial direction thereof for introducing a liquid medicine, a top portion of the handle being provided with a liquid filling port communicated with the liquid medicine cavity for a user to fill the liquid medicine;

a stamp assembly, connected with a bottom portion of the handle with a hollow cavity formed inside therein, the hollow cavity being communicated with the liquid medicine cavity for the liquid medicine to flow into and contact a microneedle, a bottom portion of the stamp assembly being provided with a needle hole, the needle hole being used for the microneedle to extend or retract;

a microneedle assembly, arranged in the hollow cavity of the stamp assembly, and including a fixing base and a plurality of microneedles, the microneedle corresponding to the needle hole of the bottom portion of the stamp assembly to ensure that the microneedle may extend from the needle hole;

a telescopic control device, arranged on the handle and in transmission connection with the microneedle assembly, the mechanical transmission structure controlling extension or retraction of the microneedle relative to the needle hole of the stamp assembly to adapt to different requirements in drug administration.

Further, the stamp assembly includes a main cavity and a bottom shell, the bottom shell is detachably connected with a bottom portion of the main cavity, and the above hollow cavity is formed between the main cavity and the bottom shell; the design of detachable structures facilitates disassembling and cleaning the inside of the hollow cavity, or to replace the bottom shell according to usage needs, such as replacing the bottom shell with a different material, such as a soft or hard bottom shell.

Further, the main cavity is detachably connected with the bottom shell by a buckle to achieve a detachable connection, wherein a slot is arranged on an inner side of a bottom portion of the main cavity, and a matching buckle is arranged on an outer side of the bottom shell; when in assembling, the buckle is aligned with the slot to press to fix the main cavity with the bottom shell; when in disassembling, the buckle is pressed inward to disengage from the slot to separate the two, so that the operation is convenient and the connection is stable.

Further, the detailed structure of the telescopic control device is as follows:

the top portion of the main cavity extends upward to form a neck portion, and the neck portion is a hollow cylindrical structure;

the telescopic control device includes a transmission member and a rotating sleeve; the transmission member is of an annular structure and is sleeved outside the neck portion; the rotating sleeve is also of the annular structure and is sleeved outside the transmission member;

an inner wall of the rotating sleeve is provided with ribs extending axially, and an outer wall of the transmission member is provided with grooves that match a shape and the number of the rib; the rib is embedded in the groove, so that when the rotating sleeve is rotated, the transmission member may be driven to rotate synchronously to avoid relative slippage between the two;

an inner wall of the transmission member is provided with an internal thread; the microneedle assembly further includes a transmission column extending upward into the neck portion, and the transmission column is provided with an external threaded portion that matches the internal thread; a side wall of the neck portion is provided with a guide groove extending along an axial direction thereof, and the external threaded portion of the transmission column passes through the guide groove and is screwed together with the internal thread of the transmission member.

The principle of telescopic control is as follows: when the rotating sleeve is rotated, the rotating sleeve drives the transmission member to rotate through the cooperation of the ribs and the grooves; since the internal thread of the transmission member is screwed together with the external threaded portion of the transmission column, and the guide groove limits the transmission column to rotate synchronously with the transmission member and only allows an axial movement, the transmission column may move axially along the guide groove to further drive the fixing base and the microneedle of the microneedle assembly to move synchronously, thereby realizing the extension or retraction of the microneedle relative to the needle hole.

Further, the fixing base includes a fixing base body and a needle base, and the needle base is detachably connected with a bottom portion of the fixing base body; the transmission column is integrally formed on a top portion of the fixing base body to ensure connection strength between the transmission column and the fixing base body; the design of the detachable structure of the needle base and the fixing base body facilitates replacing the needle base and the microneedle separately, so as to reduce the cost of use.

Further, the microneedle is fixed by a first method is as follows: a plurality of longitudinal needle plates are arranged, and "longitudinal" refers to a direction along a height of the needle base; the plurality of microneedles are grouped and fixed on a bottom edge of each of the longitudinal needle plates at a preset interval, e.g., fixing each of the needle plates with 14 microneedles; a material of the microneedle is preferably a 316L stainless steel or medical titanium alloy, and a tip of the needle is passivated; the needle base is provided with a needle plate groove that matches a shape and the number of the longitudinal needle plates, and the longitudinal needle plates are directly snapped into and fixed in the needle plate groove, so that no tools are required for installation and disassembly to facilitate quickly replacing the microneedles.

Further, the microneedle is fixed by a second method is as follows: a horizontal needle plate is arranged, and "horizontal" refers to a direction parallel to the bottom portion of the needle base; a plurality of microneedles are fixed on a bottom surface of the horizontal needle plate in a matrix, and the number of the microneedles may be one of 16, 25, 36, 49 and 100; the microneedle assembly further includes a needle pressing block, and the horizontal needle plate is pressed and fixed between the needle base and the needle pressing block; the structure may improve the stability in fixation of the microneedle and prevent the microneedle from deflecting during use.

Further, a connection relationship between the handle and the rotating sleeve is as follows: the bottom portion of the handle is inserted into the top portion of the rotating sleeve; specifically, an interference fit may be utilized, i.e., there is a protrusion on an inner wall of the rotating sleeve, which may clamp the handle to avoid shaking during use.

Further, the microneedling device further includes a catheter: one end of the catheter is communicated with a bottom portion of the liquid medicine cavity, and the other end of the catheter extends into the hollow cavity of the stamp assembly; the catheter may guide the liquid medicine to flow directly from a storage cavity into the hollow cavity, thereby preventing the liquid medicine from overflowing at a connection gap between the handle and the rotating sleeve.

Further, the liquid filling port is sealed by a method as follows: a sealing cover is detachably connected at the liquid filling port; the sealing cover and the liquid filling port may be connected with each other by threads or interference fit, and an inner side of the sealing cover may be provided with a silicone sealing ring to further enhance the sealing performance and prevent leakage of liquid medicine.

The invention has the following beneficial effects: in the invention, through the cooperation of the rotating sleeve and the transmission member, with threaded transmission and a combined structure of limiting by the guide groove of the neck portion, an extension length of the microneedle may be precisely controlled, which may be adapted to skin drug administration in multiple scenarios and improve flexibility of use.

4

Figure 1:
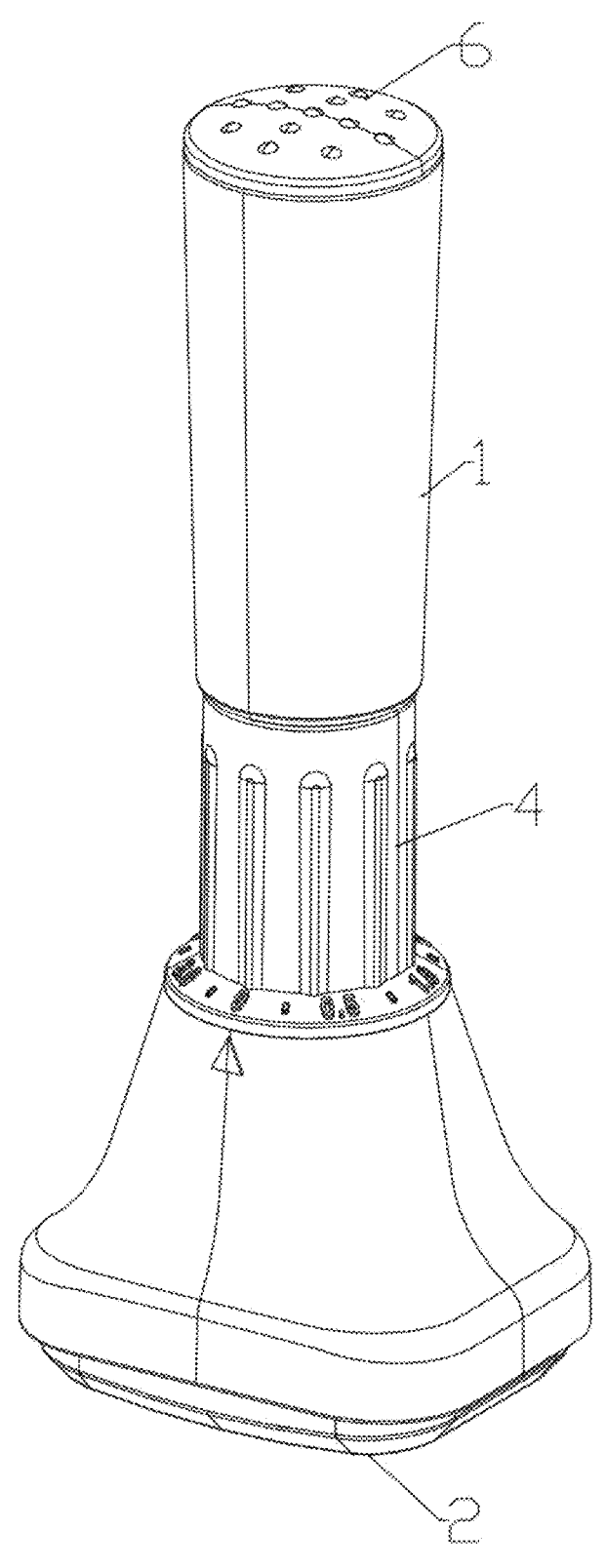
FIG. 1 is a diagram of a three-dimensional structure of the invention.
Figure 2:
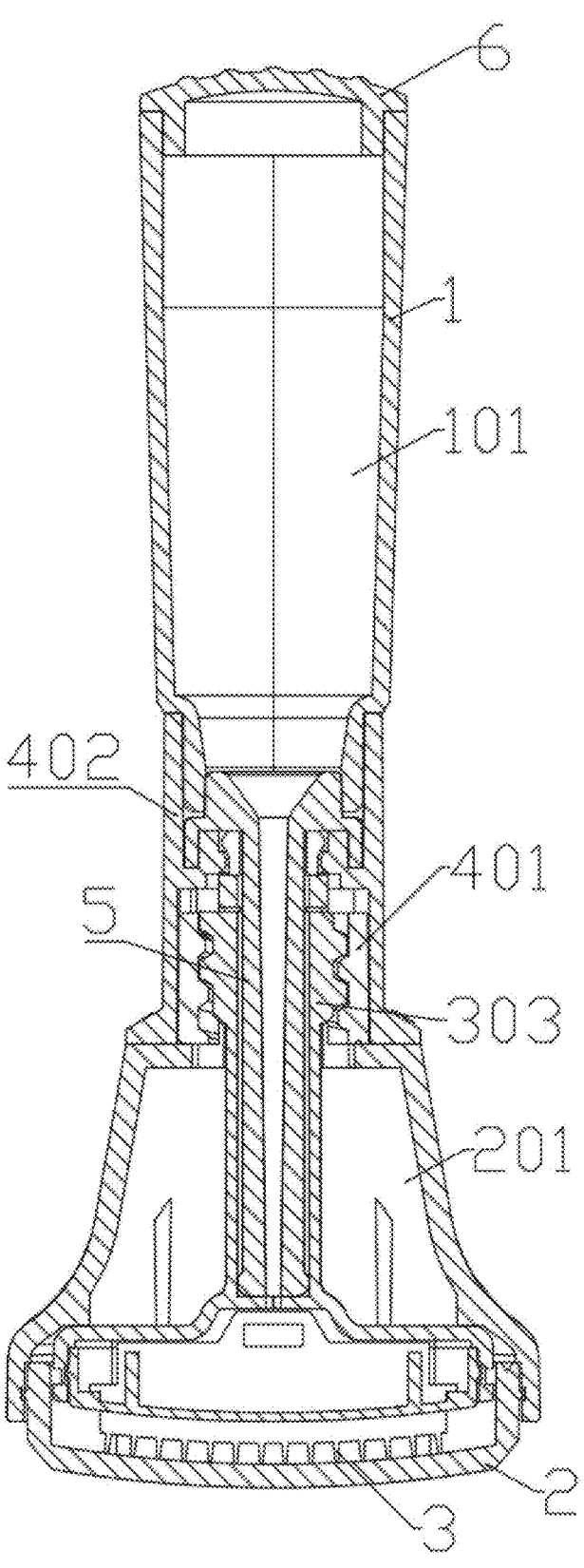
FIG. 2 is a cross-sectional diagram of the invention.
Figure 3:
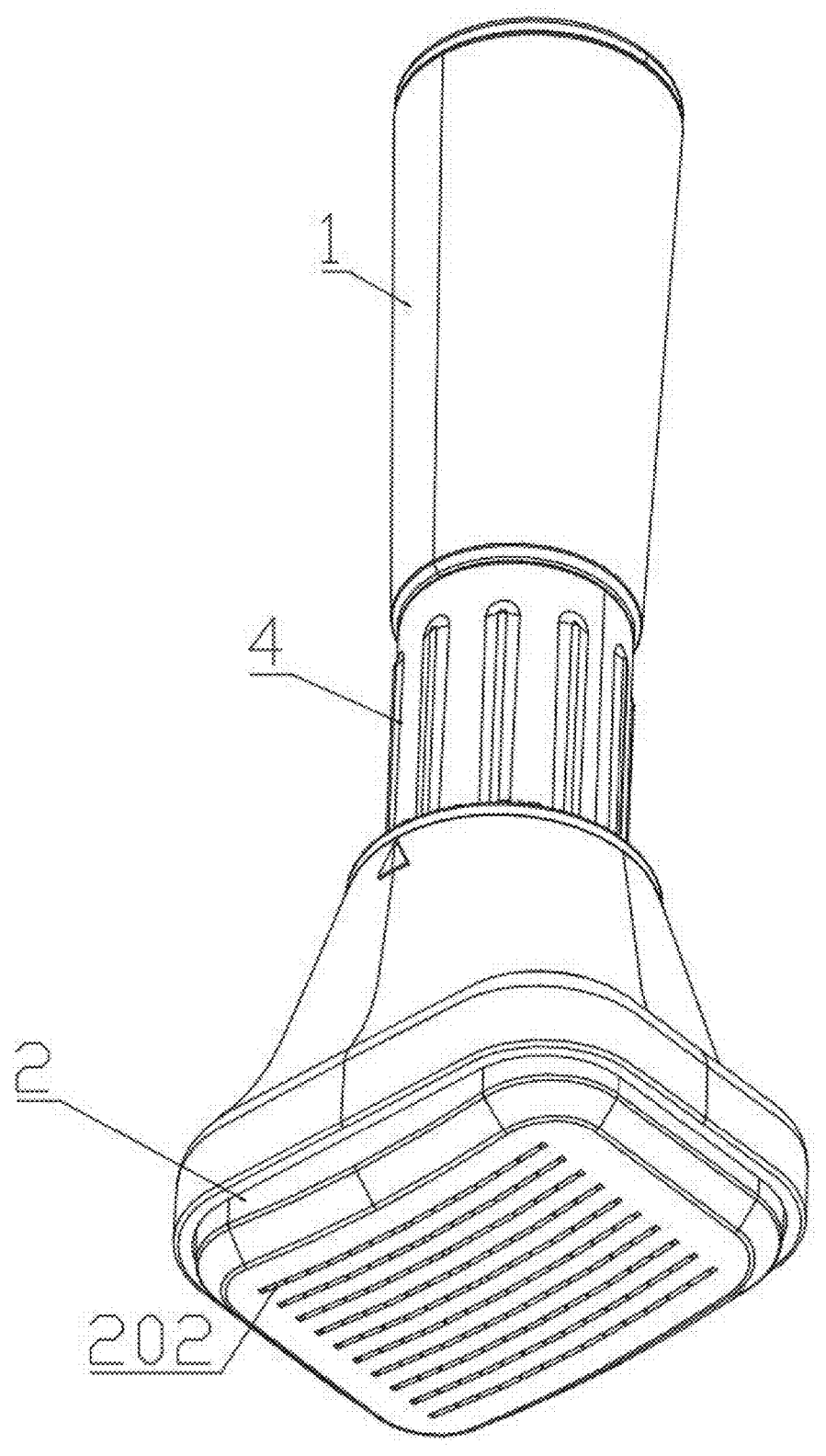
FIG. 3 is a diagram of a three-dimensional structure of the invention from a second perspective.
Figure 4:
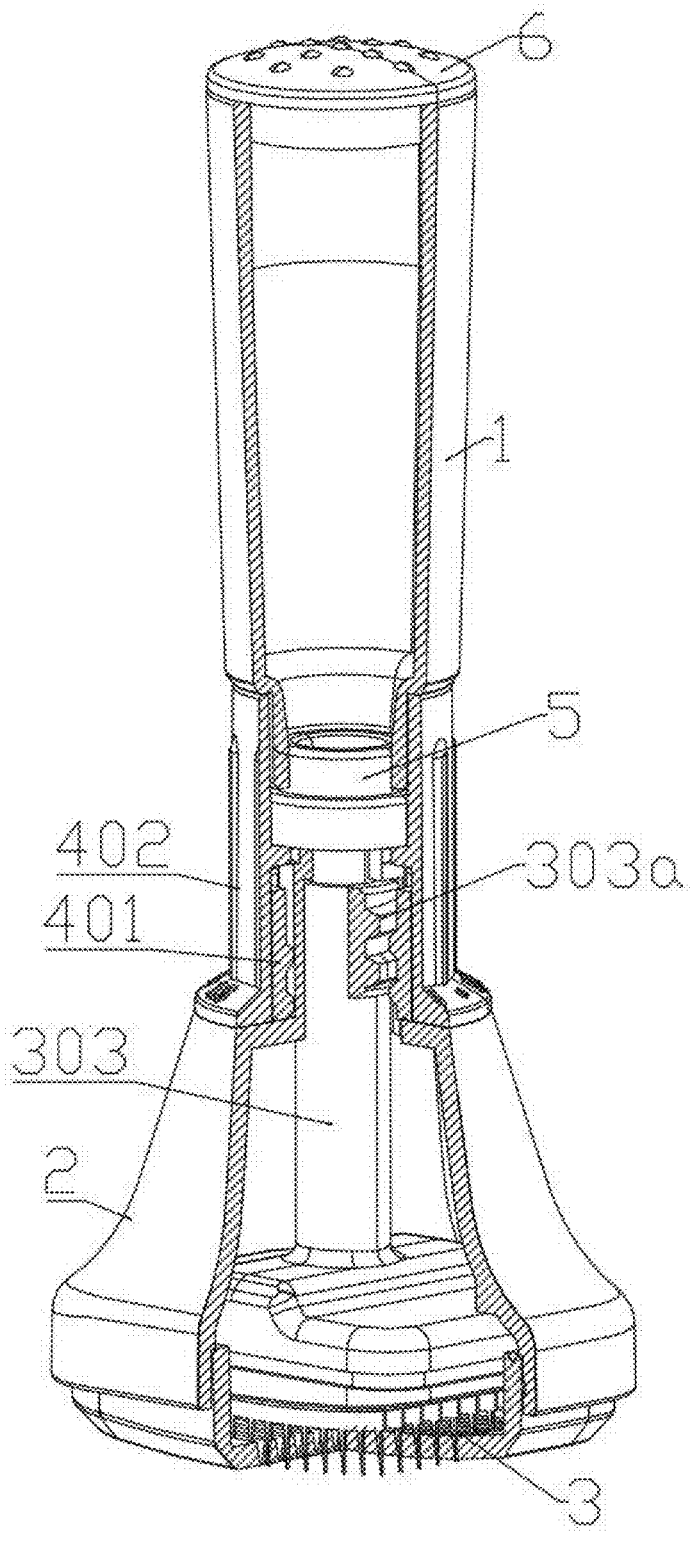
FIG. 4 is a three-dimensional cross-sectional diagram of the invention.
Figure 5:
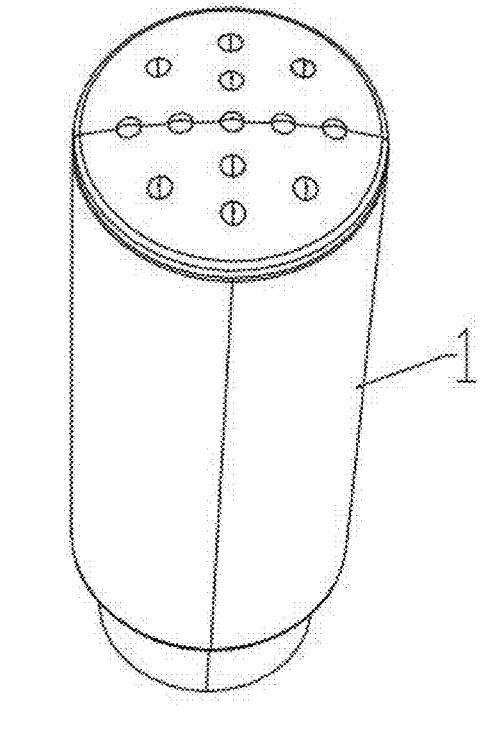
Figure 5:
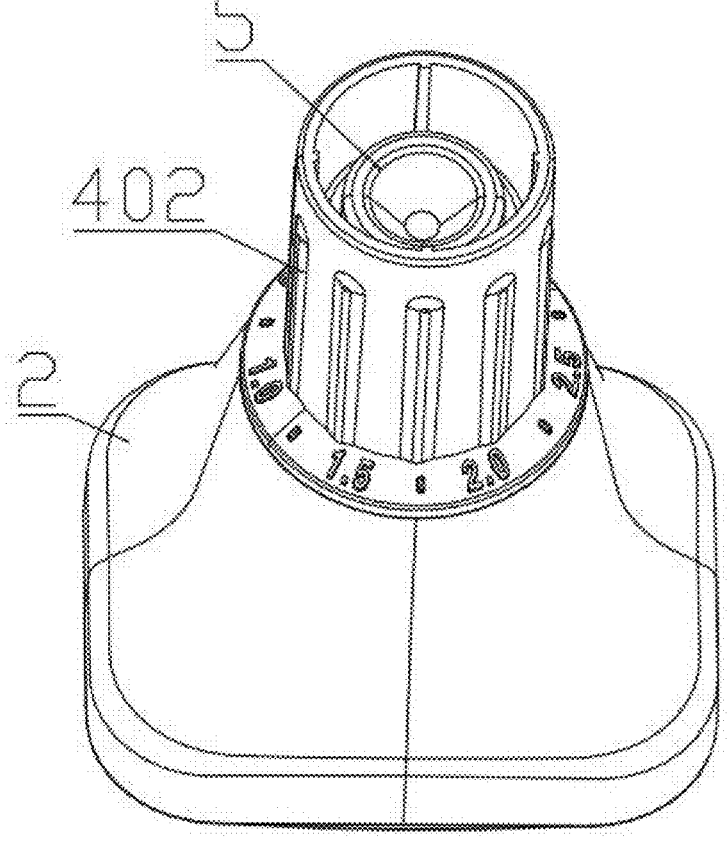
Figure 6:
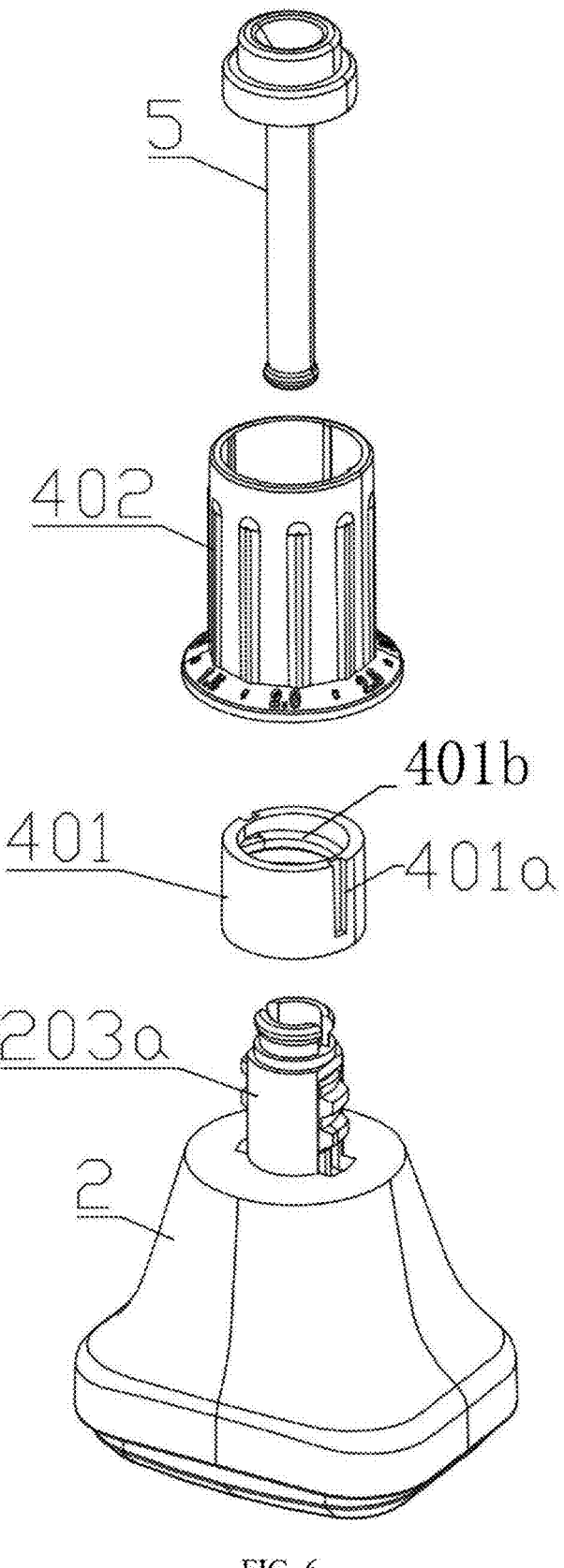
Figure 7:
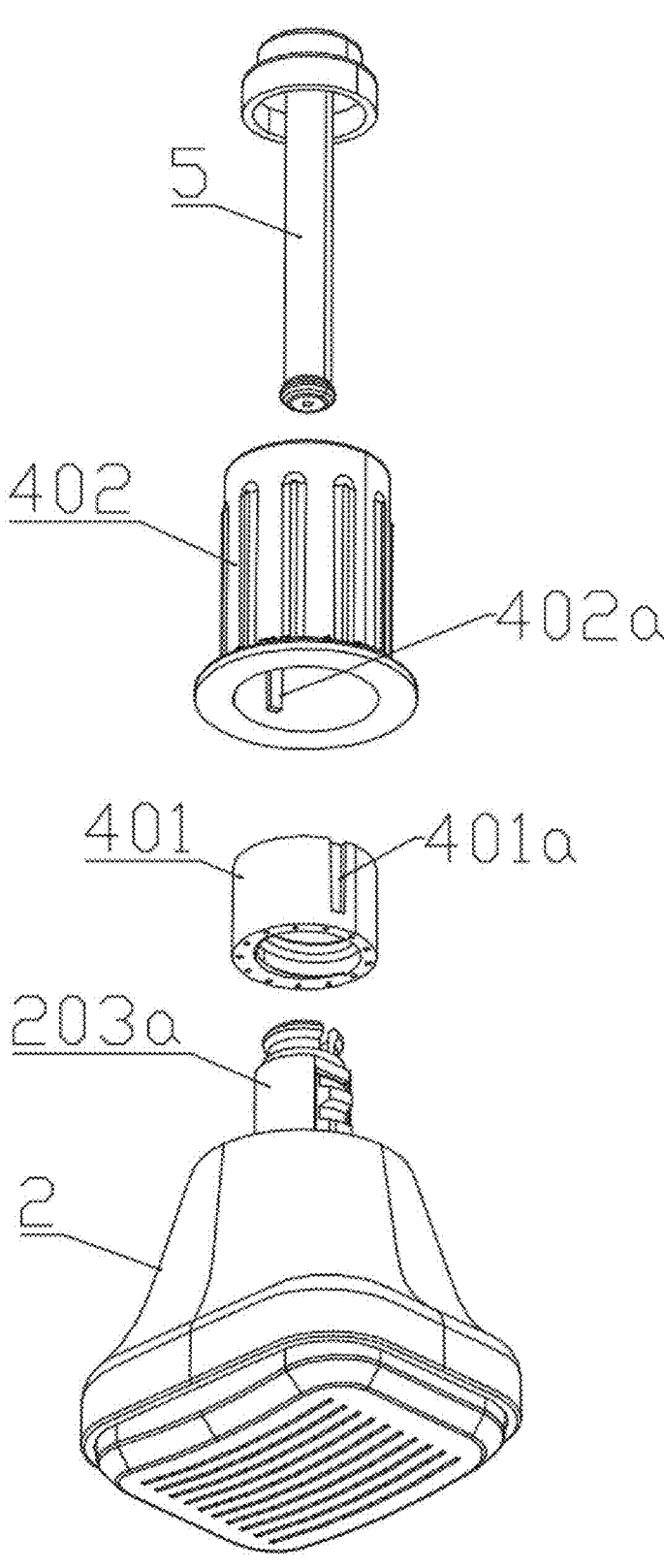
Figure 8:
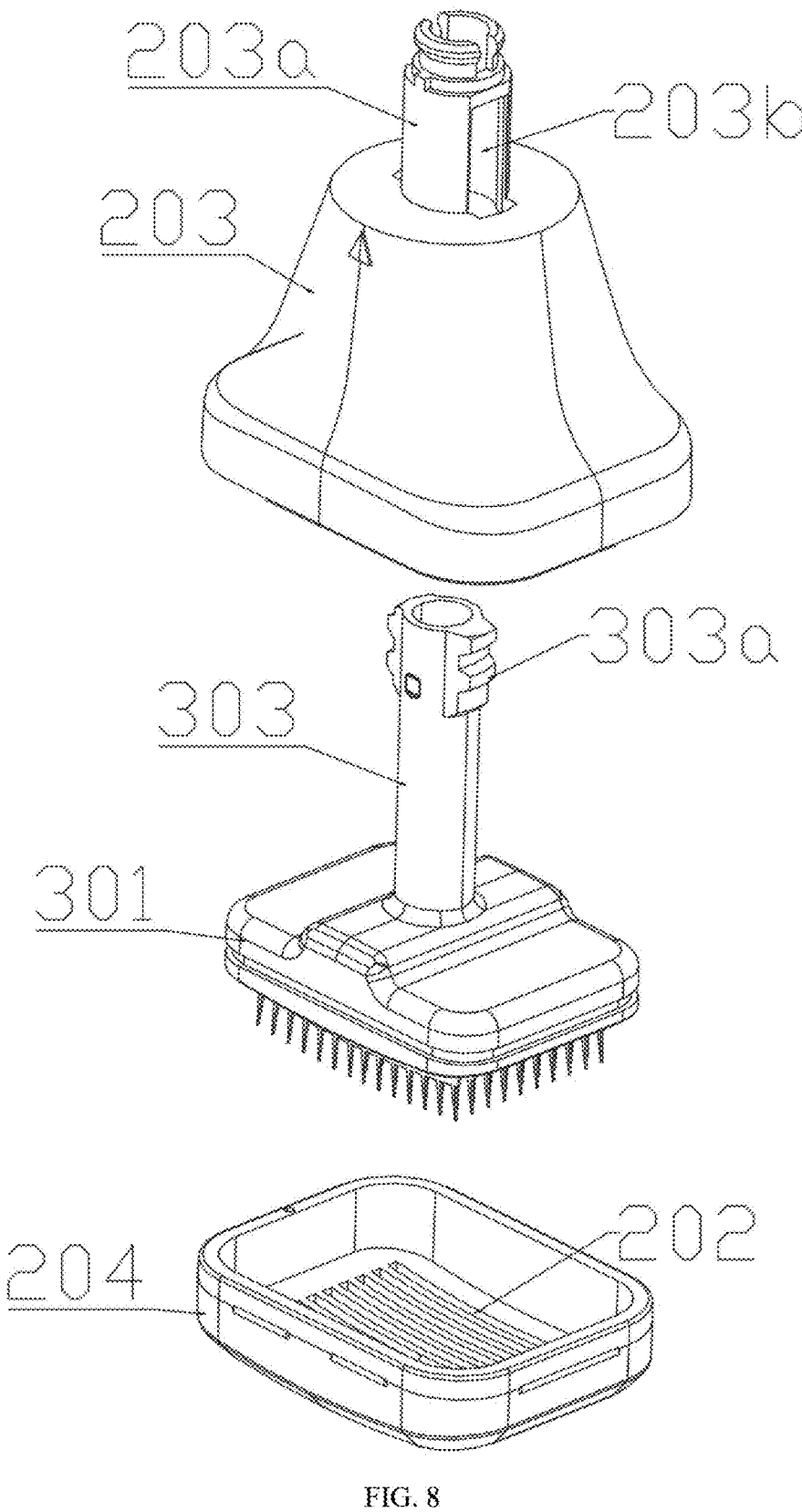
Figure 9:
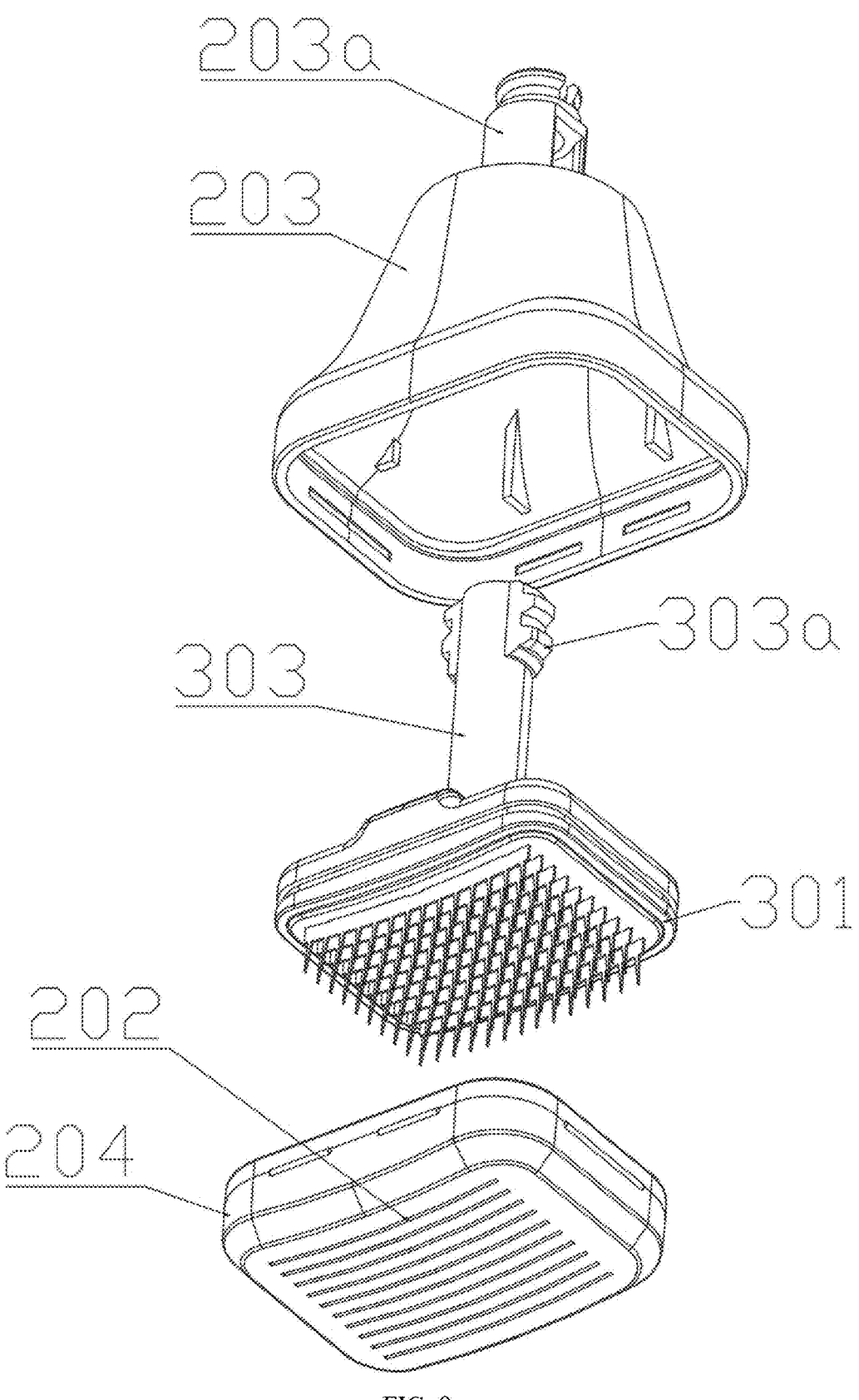
Figure 10:
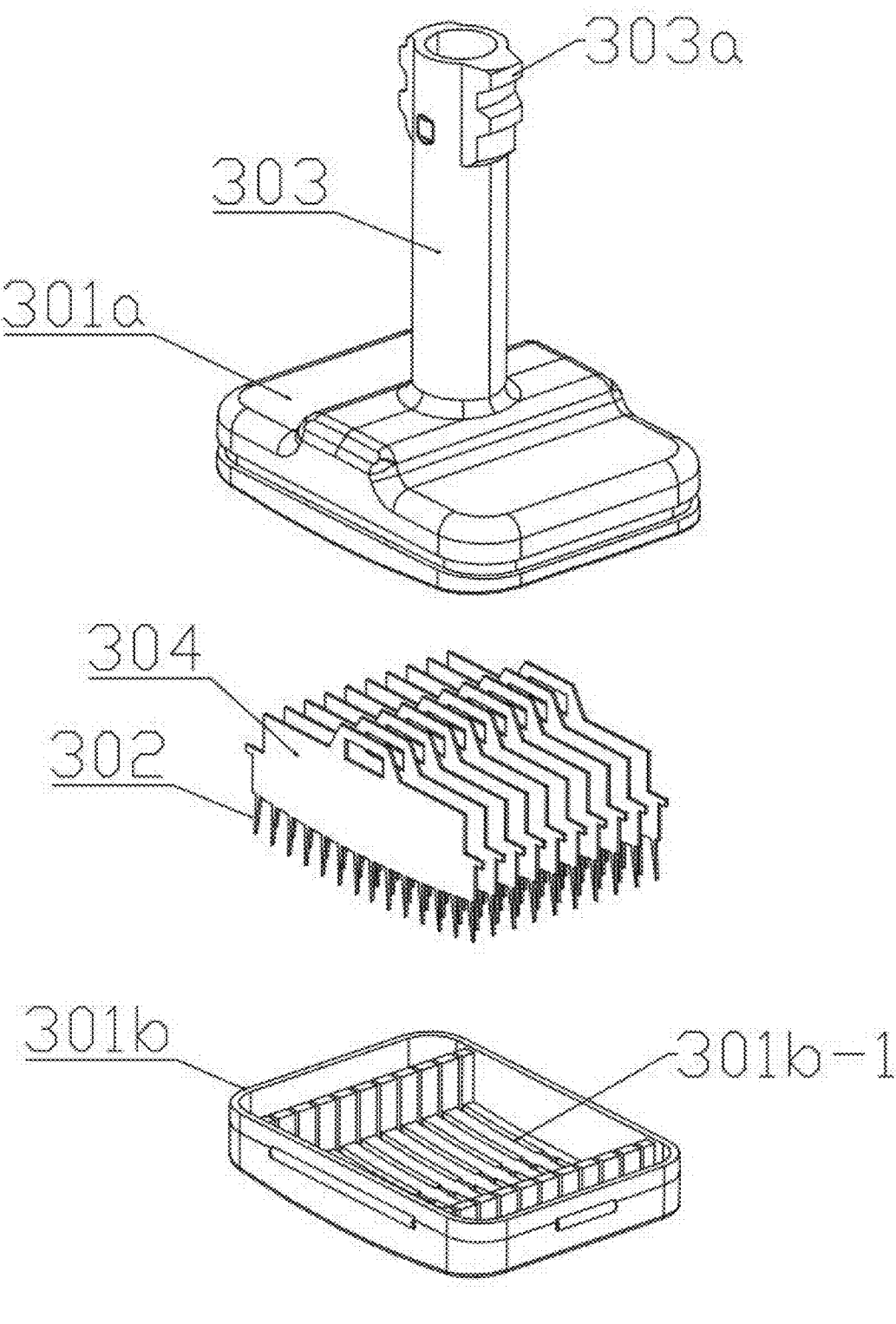
Figure 11:
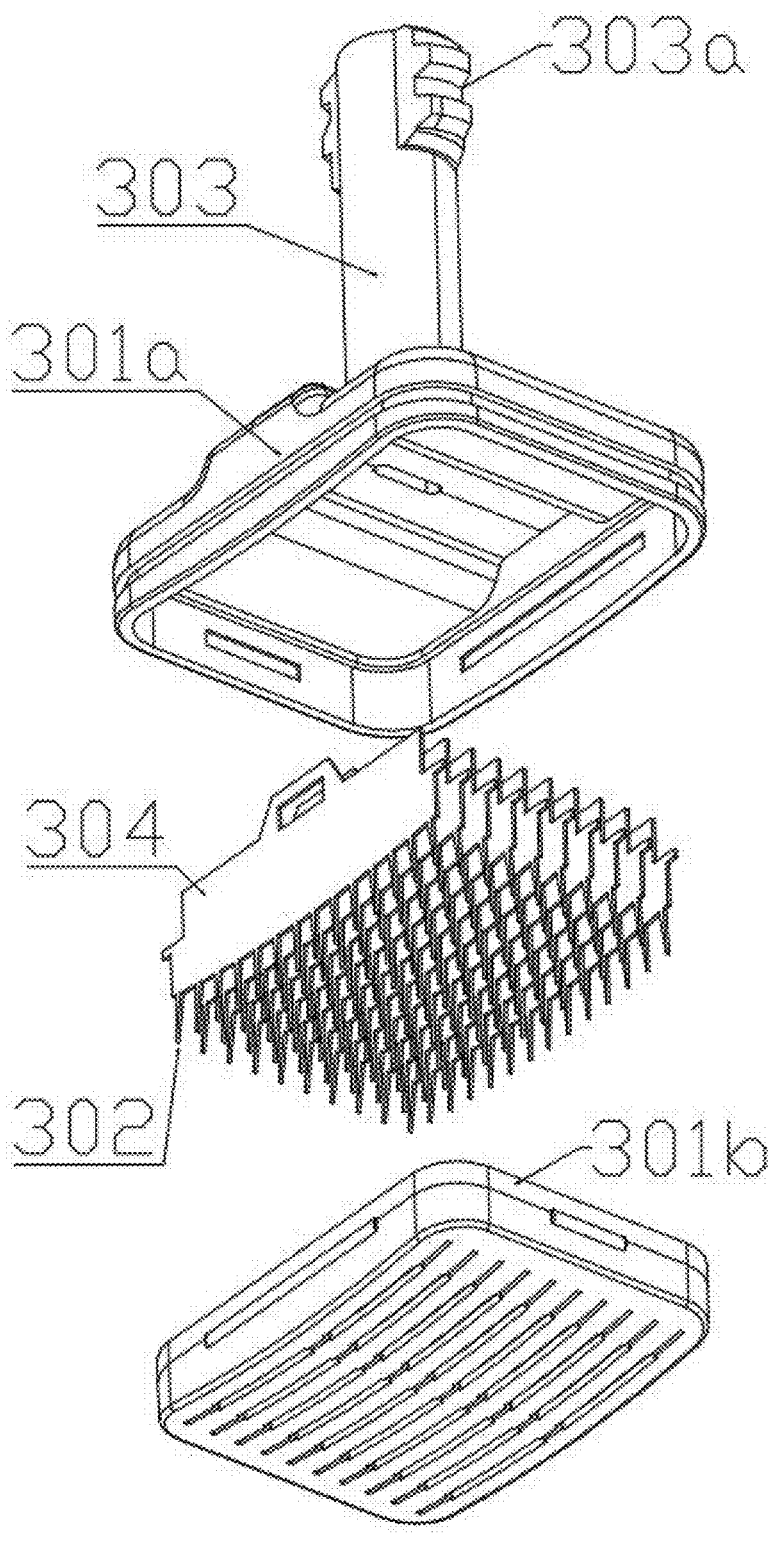
Figure 12:
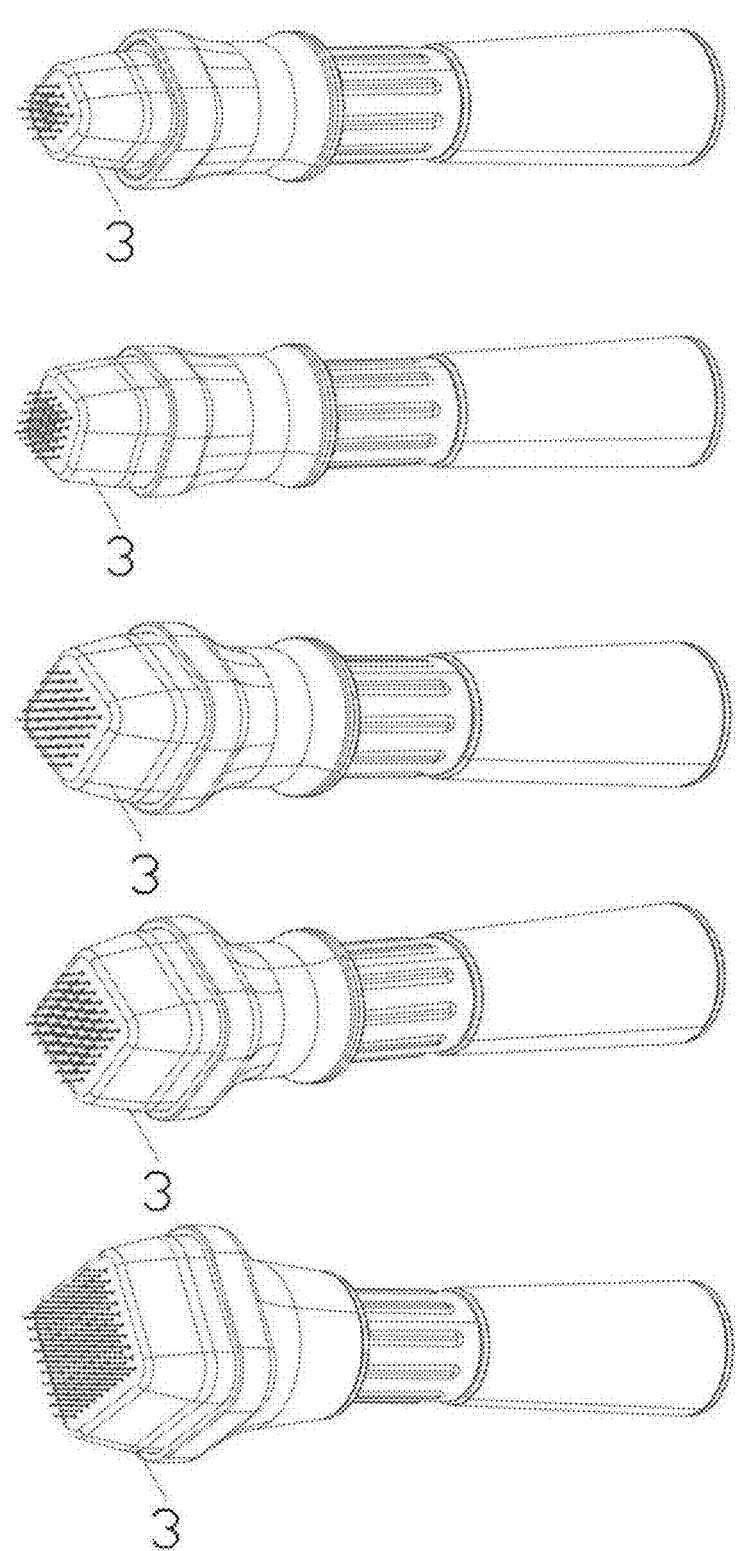
Figure 13:
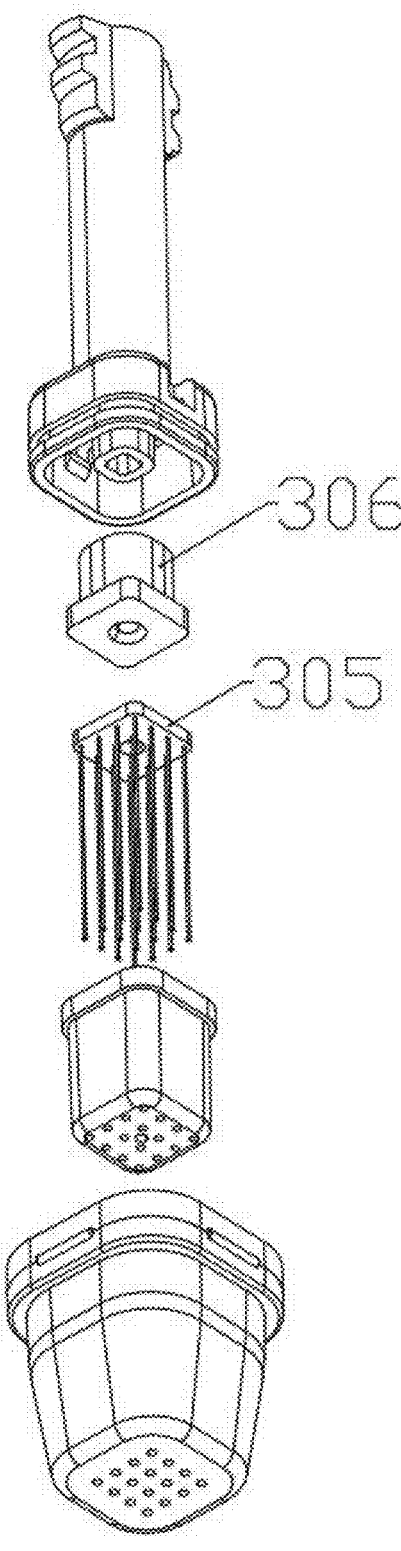
Figure 14:
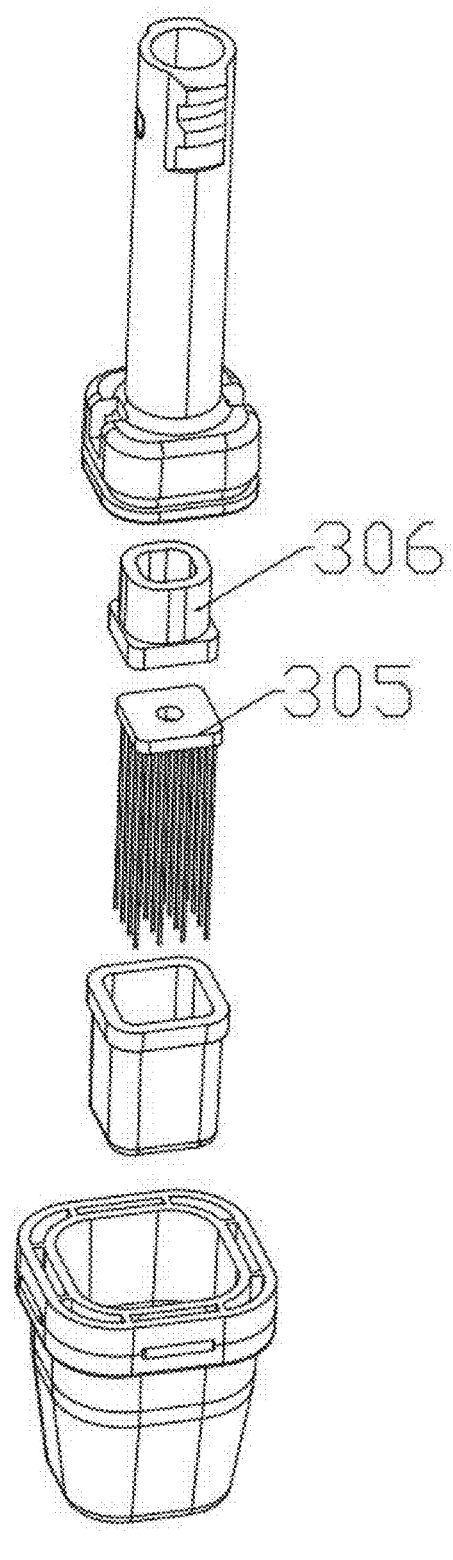

FIG. 5 is a diagram of assembling a handle according to the invention;
FIGS. 6 and 7 are diagrams of assembling a telescopic control device from different perspectives;
FIGS. 8 and 9 are diagrams of assembling a stamp assembly from different perspectives;
FIGS. 10 and 11 are diagrams of assembling a microneedle assembly from different perspectives;
FIG. 12 is a diagram of the microneedles of different numbers in Embodiment Two;
FIGS. 13 and 14 are diagrams of assembling the microneedle assembly from different perspectives in Embodiment Two;
Description of reference numerals: handle—1; liquid medicine cavity—101; stamp assembly—2; hollow cavity—201; needle hole—202; main cavity—203; neck portion—203a; guide groove—203b; bottom shell—204; microneedle assembly—3; fixing base—301; fixing base body—301a; needle base—301b; needle plate groove—301b-1; microneedle—302; transmission column—303; external threaded portion—303a; longitudinal needle plate—304; horizontal needle plate—305; needle pressing block—306; telescopic control device—4; transmission member—401; groove—401a; internal thread—401b; rotating sleeve—402; ridge—402a; catheter—5; sealing cover—6.

DETAILED DESCRIPTION OF THE EMBODIMENTS

Clear and intact description will be made on technical schemes in the embodiments of the invention below in combination with drawings in the embodiments of the invention. Obviously, the described embodiments are merely a part of embodiments of the invention and are not all the embodiments. Based on the embodiments of the present invention, all the other embodiments obtained by those of ordinary skill in the art without inventive effort are within the scope of the present invention.

Embodiment 1: A device with a longitudinal needle plate 304,
with reference to FIGS. 1 to 11, includes the following components.

A handle 1, which is a handheld operating component, is provided inside with a liquid medicine cavity 101 along an axial direction thereof for introducing a liquid medicine; a top portion of the handle is provided with a liquid filling port communicated with the liquid medicine cavity 101 for filling the liquid medicine; a sealing cover 6 is detachably connected at the liquid filling port, which may be performed by threaded connection or interference fit, and a silicone sealing ring may be arranged on the inside of the cover to prevent liquid medicine from leaking.

A stamp assembly 2 is connected with a bottom portion of the handle 1, and formed inside with a hollow cavity 201, the hollow cavity being communicated with the liquid medicine cavity 101 for the liquid medicine to flow into and contact a microneedle 302; a bottom portion of the stamp assembly is provided with a needle hole 202 for the microneedle 302 to extend or retract; the stamp assembly 2 includes a main cavity 203 and a bottom shell 204, the bottom shell 204 is detachably connected with a bottom portion of the main cavity 203, and the hollow cavity 201 is formed between the main cavity and the bottom shell, the bottom shell 204 being replaced with different materials such as soft or hard surface; a slot is arranged on an inner side of a bottom portion of the main cavity 203, and a matching buckle is arranged on an outer side of the bottom shell 204 for pressing and locking.

A microneedle assembly 3 is arranged inside the hollow cavity 201 of the stamp assembly 2 and includes a fixing base 301 and a plurality of microneedles 302, the microneedle 302 corresponding to the needle hole 202 ensure extension from the needle hole 202; the fixing base 301 includes a fixing base body 301*a* and a needle base 301*b*, and the needle base 301*b* may be detachably connected with a bottom portion of the fixing base body 301*a* so that the needle base 301*b* and the microneedle 302 may be replaced separately; a transmission column 303 is integrally formed on a top portion of the fixing base body 301*a*, and the transmission column 303 extends upward into the neck portion 203*a*; the microneedle 302 is fixed through a longitudinal needle plate 304, and "longitudinal" refers to a direction along a height of the needle base 301*b*, a plurality of microneedles 302 being grouped and fixed at a bottom edge of each longitudinal needle plate 304 at a preset interval (e.g., each needle plate may be fixed with 14 microneedles 302), a material being preferably a 316L stainless steel or medical titanium alloy, a tip of the needle being passivated; the needle base 301*b* is provided with a needle plate groove 301*b*-1 matching the longitudinal needle plate 304, and the longitudinal needle plate 304 is directly engaged and fixed in the groove.

A telescopic control device 4 is arranged on the handle 1 and is in transmission connection with the microneedle assembly 3; the top portion of the main cavity 203 extends upward to form a neck portion 203*a*; the telescopic control device includes a transmission member 401 and a rotating sleeve 402, the transmission member 401 and the rotating sleeve 402 are both of annular structures, the transmission member 401 is sleeved outside the neck portion 203*a*, and the rotating sleeve 402 is arranged outside the transmission member 401; an inner wall of the rotating sleeve 402 is provided with an axially-extending rib 402*a*, and an outer wall of the transmission member 401 is provided with a matching groove 401*a*, the rib 402*a* being embedded in the groove 401*a*, the rotating sleeve 402 driving the transmission member 401 to rotate synchronously to prevent slipping; an inner wall of the transmission member 401 is provided with an internal thread 401*b*, and the transmission column 303 is provided with a matching external threaded portion 303*a*; a side wall of the neck portion 203*a* is provided with an axially-extending guide groove 203*b*; when the rotating sleeve 402 is rotated, the transmission member 401 is driven to rotate, and through the threaded engagement and the limitation of the guide groove 203*b*, the transmission column 303 moves axially along the guide groove 203*b* to drive the microneedle 302 to extend/retract.

A catheter 5 has one end connected to a bottom portion of the liquid medicine cavity 101 and the other end extending into the hollow cavity 201 of the stamp assembly 2, which may guide the liquid medicine to flow directly into the hollow cavity 201 and prevent the liquid medicine from overflowing from a gap between the handle 1 and the rotating sleeve 402.

The handle 1 is connected with the rotating sleeve 402, and the bottom portion of the handle 1 is inserted into a top portion of the rotating sleeve 402 with an interference fit. An inner wall of the rotating sleeve 402 is provided with a protrusion to clamp the handle 1 to prevent shaking during use.

Assembly steps are based on the instructions.

Installation of the catheter 5: one end of the catheter 5 is connected with the bottom portion of the liquid medicine cavity 101, and the other end thereof is passed through the bottom portion of the handle 1 and extended into the hollow cavity 201 of the stamp assembly 2 to be assembled later.

Assembly of the telescopic control device 4 and the stamp assembly 2:

the external threaded portion 303*a* of the transmission column 303 is passed through the guide groove 203*b* of the neck portion 203*a*, so that the fixing base body 301*a* is placed in the main cavity 203;

the transmission member 401 is sleeved outside the neck portion 203*a*, so that the internal thread 401*b* on the inner wall of the transmission member 401 is screwed into the external threaded portion 303*a* of the transmission column 303;

the rotating sleeve 402 is sleeved outside the transmission member 401 to ensure that the ridge 402*a* of the inner wall of the rotating sleeve 402 is embedded in the groove of the outer wall of the transmission member 401.

Connection of the handle 1 and the rotating sleeve 402: the bottom portion of the handle 1 is inserted into the top portion of the rotating sleeve 402, and the handle 1 is clamped through the interference fit of the protrusion on the inner wall of the rotating sleeve 402.

Installation of the microneedle assembly 3: the longitudinal needle plate 304 is engaged and fixed in the needle plate groove 301*b*-1 of the needle base 301*b*, and then the needle base 301*b* is detachably connected with the bottom portion of the fixing base body 301*a*.

Sealing of the stamp assembly 2 and addition of the liquid medicine: the buckle at the outer side of the bottom shell 204 is aligned with the slot at the inner side of the bottom portion of the main cavity 203, pressed and engaged to fix; the sealing cover 6 of the liquid filling port is opened to add the liquid medicine to the liquid medicine cavity 101, and then the sealing cover 6 is closed to seal.

The steps for using the microneedle device are as follows.

1. Pretreatment: the skin area is cleaned to be medicated, and the bottom surface of the bottom shell 204 of the stamp assembly 2 is disinfected.

2. Positioning and extension of the microneedle 302: the handle 1 is held by hands to rotate the rotating sleeve 402 to drive the microneedle 302 to extend from the needle hole 202 through the telescopic control device 4, wherein the extension length may be adjusted according to the skin conditions and requirements in drug administration.

3. Introduction of the liquid medicine: the liquid medicine in the liquid medicine cavity 101 flows into the hollow cavity 201 of the stamp assembly 2 through the catheter 5, and then penetrates into the skin along the microneedle 302 after contacting the microneedle 302.

4. Recycling and cleaning of the microneedle 302: the rotating sleeve 402 is rotated in the opposite direction to retract the microneedle 302 into the hollow cavity 201; the bottom shell 204 and the needle base 301*b* are removed, and the hollow cavity 201, the bottom shell 204, the needle base 301*b* and the longitudinal needle plate 304 are cleaned, or the needle base 301*b*/the longitudinal needle plate 304 are replaced for future use.

Embodiment 2: Microneedle device with horizontal needle plate 305 With reference to FIGS. 12 to 14, the only difference between the embodiment and Embodiment 1 lies in the microneedles 302 of the microneedle assembly 3 and the way the microneedles 302 are fixed, as well as the adaptive changes in shape and size made by the changes in the microneedles 302 and the way the microneedles 302 are fixed; the structure, and the structure, connection relationship and assembly/use logic of the remaining assemblies are consistent with those in Embodiment 1.

For the microneedle assembly 3, specific differences are as follows: the microneedles 302 are fixed by the horizontal needle plate 305, and "horizontal" refers to a direction parallel to the bottom portion of the needle base 301*b*, a plurality of microneedles 302 being fixed to the bottom surface of the horizontal needle plate 305 as a whole in a matrix, the number of microneedles 302 being selected from 16, 25, 36, 49 and 100;

the microneedle assembly 3 further includes a needle pressing block 306, the horizontal needle plate 305 is pressed and fixed between the needle base 301*b* and the needle pressing block 306 through the needle pressing block 306, thereby improving the stability in fixation of the microneedles 302 and preventing the same from deflecting during use.

Although the embodiments of the present invention have been shown and described, it can be understood that a person skilled in the art can make various changes, modifications, substitutions and variations to the embodiments without departing from the principle and spirit of the present invention; and the scope of the present invention is defined by the attached claims and equivalents thereof.

What is claimed is:

1. A microneedling device, comprising:
a handle (1), a liquid medicine cavity (101) being arranged inside the handle (1), a top portion of the handle (1) being provided with a liquid filling port communicated with the liquid medicine cavity (101);
a stamp assembly (2), the stamp assembly (2) being connected with a bottom portion of the handle (1) and provided inside with a hollow cavity (201), the hollow cavity (201) being communicated with the liquid medicine cavity (101), a bottom portion of the stamp assembly (2) being provided with a needle hole (202);
a microneedle assembly (3), the microneedle assembly (3) being arranged inside the hollow cavity (201), the microneedle assembly (3) comprising a fixing base (301) and a plurality of microneedles (302), each of the plurality of microneedle (302) corresponding to the needle hole (202);
a telescopic control device (4), the telescopic control device (4) being arranged on the handle (1), the telescopic control device (4) being in transmission connection with the microneedle assembly (3) for controlling the microneedle (302) to extend or retract relative to the needle hole (202) of the stamp assembly (2);
the stamp assembly (2) comprises a main cavity (203) and a bottom shell (204) detachably connected with a bottom portion of the main cavity (203), and the hollow cavity (201) is formed between the main cavity (203) and the bottom shell (204);
the main cavity (203) is detachably connected with the bottom shell (204) by a buckle to achieve a detachable connection;
a top portion of the main cavity (203) extends upward to form a neck portion (203*a*);
the telescopic control device (4) comprises a transmission member (401) and a rotating sleeve (402);
the transmission member (401) is sleeved outside the neck portion (203*a*);
the rotating sleeve (402) is sleeved outside the transmission member (401), an inner wall of the rotating sleeve (402) is provided with a ridge (402*a*), and an outer wall of the transmission member (401) is provided with a groove (401*a*) that matches the ridge (402*a*) so that the rotating sleeve (402) may drive the transmission member (401) to rotate synchronously;
an inner wall of the transmission member (401) is provided with an internal thread (401*b*);
the microneedle assembly (3) further comprises a transmission column (303) extending upward into the neck portion (203*a*), and the transmission column (303) is provided with an external threaded portion (303*a*);
the neck portion (203*a*) is provided with a guide groove (203*b*) extending along an axial direction thereof, and the external threaded portion (303*a*) of the transmission column (303) passes through the guide groove (203*b*) and is screwed together with the internal thread (401*b*) of the transmission member (401);
by rotating the rotating sleeve (402), the transmission member (401) may be driven to rotate, and then the transmission column (303) is driven to move axially along the guide groove (203*b*) through the cooperation between the internal thread (401*b*) and the external threaded portion (303*a*), so as to achieve the extension or retraction of the microneedle (302);
one end of the transmission member (401) and one end of the rotating sleeve (402) are in contact with one end of the main cavity (203) of the stamp assembly (2).

2. The microneedling device according to claim 1, wherein the fixing base (301) of the microneedle assembly (3) comprises a fixing base body (301*a*) and a needle base (301*b*) detachably connected with a bottom portion of the fixing base body (301*a*), and the transmission column (303) is integrally formed on a top portion of the fixing base body (301*a*).

3. The microneedling device according to claim 2, wherein the microneedle assembly (3) is provided with a plurality of longitudinal needle plates (304), the plurality of microneedles (302) are grouped and fixed on bottom edges of the plurality of longitudinal needle plates (304), and the longitudinal needle plates (304) are snap-fitted and fixed on the needle base (301*b*); the needle base (301*b*) is provided with a needle plate groove (301*b*-1) that matches the longitudinal needle plate (304).

4. The microneedling device according to claim 2, wherein a horizontal needle plate (305) is arranged, and the plurality of microneedles (302) are fixed as a whole on a bottom surface of the horizontal needle plate (305); the microneedle assembly (3) further comprises a needle pressing block (306), and the horizontal needle plate (305) is pressed and fixed on the needle base (301*b*) by the needle pressing block (306).

5. The microneedling device according to claim 1, wherein the bottom portion of the handle (1) is inserted into a top portion of the rotating sleeve (402).

6. The microneedling device according to claim 5, comprising a catheter (5), wherein one end of the catheter (5) is communicated with a bottom portion of the liquid medicine cavity (101), and the other end of the catheter extends into the hollow cavity (201) of the stamp assembly (2) and is communicated with the microneedle assembly (3) in the hollow cavity (201).

7. The microneedling device according to claim 1, wherein a sealing cover (6) is detachably connected at the liquid filling port.

\* \* \* \* \*